United States Patent [19]

Breglio et al.

[11] 4,454,232

[45] Jun. 12, 1984

[54] ESTRIOL ASSAY

[75] Inventors: Susan E. Breglio, Pinole; Mark S. Hanamoto, Mill Valley, both of Calif.

[73] Assignee: Bio-Rad Laboratories, Inc., Richmond, Calif.

[21] Appl. No.: 385,598

[22] Filed: Jun. 7, 1982

[51] Int. Cl.³ .................... G01N 33/54; G01N 33/58; G01N 33/60

[52] U.S. Cl. .................... 436/504; 436/542; 436/800; 436/804; 436/826

[58] Field of Search .................. 424/1; 436/504, 542, 436/800, 804, 826

[56] References Cited

U.S. PATENT DOCUMENTS

| | | | |
|---|---|---|---|
| 3,997,470 | 12/1976 | Monte et al. | 252/408 |
| 4,107,284 | 8/1978 | Sultanian et al. | 436/500 |
| 4,128,629 | 12/1978 | Eldred et al. | 424/1 |
| 4,166,103 | 8/1979 | Wagner et al. | 424/1 |
| 4,208,400 | 1/1980 | Edwards | 424/1 |
| 4,366,143 | 12/1982 | Midgley et al. | 436/504 |

OTHER PUBLICATIONS

Evans et al., Clin. Chim. Acta, 114 (1981), 309–313.

Fowler et al., Chemical Abstracts, vol. 90, (1979), Abstract 199783u.

*Primary Examiner*—Christine M. Nucker
*Attorney, Agent, or Firm*—Townsend & Townsend

[57] ABSTRACT

An improved immunoassay technique for determining the presence of estriol in human sera comprises adding preselected amounts of a non-ionic detergent and a surface active agent to the assay medium to lessen inaccuracies resulting from variable serum protein concentrations in the sample.

18 Claims, No Drawings

ESTRIOL ASSAY

BACKGROUND OF THE INVENTION

1. Field of the Invention

The present invention relates generally to immunoassays for the detection of estriol in human serum and, more particularly, relates to an improved assay method which corrects certain inaccuracies which have been observed in the assay of serum samples having variable serum protein concentration.

Estriol is the principle circulating estrogen of pregnancy. The adrenal medulla of the fetus provides the bulk of the estriol precursors. These precursors are then metabolized to estriol in the placenta, where they are passed into the maternal circulation. Estriol exists in the maternal blood as a mixture of the unconjugated form together with a number of conjugates.

The level of unconjugated estriol increases during the course of pregnancy and does not reach a plateau until late in pregnancy. A decreasing level may be associated with fetal distress. Serial determination of estriol levels may be used as one monitor of fetal distress during high risk pregnancies, e.g., those which involve diabetes, hypertension or toxemia. Failure to exhibit a steady increase in unconjugated estriol, as well as total estriol, can indicate the impairment of fetal well being. Thus, it is highlydesirable to provide a convenient and accurate assay for the presence of estriol in the serum of pregnant human females.

2. Description of the Prior Art

Immunoassays for the determination of estriol in human serum are known. One such technique, based on the principle of radioimmunoassay (RIA), relies upon competitive binding between the native estriol in the patient's serum, if any, and radioactively labeled estriol, which is added to the serum. The labeled and non-labeled species compete to bind with immobilized anti-estriol antibodies covalently coupled to insoluble polymer beads. After incubation, the beads are separated from the free labeled species and the radioactivity associated with the beads is counted. By using a standard curve, the concentration of estriol in the patient's sample may be determined.

Although generally accurate, it has been observed that the above-described assay technique yields inaccurate results in sera having protein concentrations other than normal (referred to herein as "variable" protein concentrations). In particular, it is observed herein that when compared to standards having normal protein concentrations, samples having low serum protein levels exhibit a higher degree of binding between the labeled estriol and the immobilized anti-estriol antibodies when no estriol is present in the sample. This "protein effect" is carried over to serum samples having positive levels of estriol, yielding apparent estriol levels which are lower than the actual estriol levels in the blood. It is thus desirable to provide an improved assay method which will give accurate results in all patients' sera, regardless of the protein concentration in a particular sera.

SUMMARY OF THE INVENTION

The present invention overcomes the observed protein effect by adding a combination of a non-ionic detergent and a surface active agent to the assay medium. It has been found that the use of these additives in combination substantially eliminates the variable binding of labeled estriol to anti-estriol in immunoassays of serum samples having variable protein concentrations. Suitable non-ionic detergents include polyoxyethylene ethers. Suitable surface active agents include polyoxyethylenesorbitans, deoxycholate salts such as sodium deoxycholate, and ANS (8-anilino-1-napthalenesulfonic acid).

DESCRIPTION OF THE PREFERRED EMBODIMENT

1. Method

The present invention provides an improved immunoassay for determining the presence of estriol in a sample of human serum. The invention relies on the addition of a non-ionic detergent and a surface active agent to the assay medium to lessen or eliminate inaccuracies which result from differing binding kinetics between estriol and anti-estriol in serum samples having variable protein concentrations when compared with samples having normal protein levels.

A wide variety of assay protocols may be employed, including competitive and non-competitive techniques, and the present invention is not limited to any particular technique. For example, native estriol and labeled estriol may compete for binding to anti-estriol antibody where the degree of binding of the labeled estriol is inversely related to the amount of estriol in the sample. Other suitable assay protocols are well known in the art and need not be described further.

The present invention is also compatible with virtually all labeling systems presently employed in immunoassays. These include, most commonly, radioimmunoassay (RIA), enzyme immunoassay (EIA), fluorescent labeling systems, bacteriophage systems, and the like. Extensive literature is available concerning such systems.

The assay method of the present invention is, however, limited to immunoassays involving the specific binding between estriol and a specific binding protein. It has been found that the degree of binding between estriol and anti-estriol antibody in such assays can be affected by the level of serum proteins in the sample being tested. Specifically, low serum protein concentrations (i.e., below about 7%) lead to increased binding between the estriol species, including both native estriol and labeled estriol, to the immobilized anti-estriol antibody. The exact reasons for this "protein effect" are unknown. The effect can, however, adversely affect the performance of an immunoassay, particularly when the results of individual assays are compared to a standard curve. In that case, the absolute amount of binding between the labeled reagent and the solid phase is affected both by the concentration of estriol in the sample and by the serum protein concentration. Since these effects cannot be separated, errors are introduced in the individual readings.

The preferred embodiment is a competitive binding assay utilizing radioactively labeled estriol and antiestriol antibody immobilized on a separable solid phase, typically insoluble polymeric beads. The sample, the immobilized anti-estriol antibody, and the labeled estriol are combined in any convenient manner and allowed to incubate, typically for at least one hour. After incubation, the beads are separated by centrifugation and the supernatants are carefully removed. The beads are then counted by a suitable radioactive decay monitor and the results recorded. In addition to the unknown samples, a plurality of known standards are concurrently run to generate a standard curve for calibration of the assay.

According to the present invention, a non-ionic detergent selected from the group comprising polyoxyethylene ethers and a surface active agent selected from the group comprising polyoxyethylenesorbitans, sodium deoxycholate, and ANS (8-anilino-1-napthalenesulfonic acid) are added to the assay medium at concentrations effective to inhibit the protein effect without adversely affecting the results in samples having normal protein concentrations. The preferred concentrations are as follows:

| | Concentrations ($\mu$g/ml) | |
|---|---|---|
| | Broad Range | Narrow Range |
| Non-ionic Detergent | 30–1500 | 270–330 |
| Surface Active Agent | | |
| Polyoxyethylenesorbitan | 100–5000 | 500–2500 |
| Sodium Deoxycholate | 100–5000 | 500–2500 |
| ANS | 1–100 | 10–25 |

The additives should be introduced to the assay medium prior to or concurrently with the combination of the immobilized anti-estriol, the sample and the labeled estriol. Conveniently, the additives may be mixed and stored with the labeled estriol in a buffer solution, as will be described hereinafter. Alternatively, either or both of the additives could be stored and added separately to the assay medium, or combined and stored with the solid phase reagent.

2. Materials

The non-ionic detergent typically includes a non-dissociated hydrophilic group, usually containing a multiplicity of oxygen functions, such as ethers or alcohols, which engage in polar interactions with the aqueous solution. Suitable non-ionic detergents include ethers derived from fatty acids and sugars, such as polyoxyethylene ethers including lauryl ether, cetyl ether, oleyl ether, stearyl ether, and, tridecyl ether. Such polyoxyethylene ethers are available under the tradename Brij ® from Sigma Chemical Company, St. Louis, Mo.

The surface active agent is selected from the group comprising deoxycholate salts; ANS; and polyoxyethylenesorbitans, such as polyoxyethylenesorbitan mono-laurate, polyoxyethylenesorbitan mono-palmitate, polyoxyethylenesorbitan mono-stearate, and polyoxyethylenesorbitan trioleate. The polyoxyethylenesorbitans may be derived as esters of sorbitol and its anhydrides copolymerized with excess ethylene oxide. Such polyoxythylenesorbitans are available under the tradename Tween ® from Rohm & Hass, Philadelphia, Pa.

The remaining materials utilized will depend on the protocol to be employed. Generally, anti-estriol antibody will be employed together with either labeled estriol, for competitive binding techniques. Various ancillary reagents, such as buffers, preservatives, and the like, will also find use.

Conveniently, the additives will be combined with either the labeled estriol or with the immobilized receptor for storage prior to use, although the additives may be stored separately. The prepared reagents may be stored in buffer solution, or lyophilized and reconstituted prior to use, as desired. The storage of such immunological reagents is well known in the art and need not be discussed further.

EXPERIMENTAL RESULTS

The following reagents were employed. All percentages are by weight.

Tracer—Radioactively labeled ($^{125}$I less than 10$\mu$Ci/100ml) estriol in 0.1M borate buffer, 0.05% gelatin and 0.01% sodium azide at pH 8.5.

Beads—Polyacrylamide beads having rabbit antiestriol antibody covalently coupled thereto in 0.1M phosphate buffer, 0.05% gelatin and 0.01% sodium azide at pH 7.5.

Referring to Table 1, fourteen samples having differing concentrations of serum proteins and estriol were assayed. Three of the samples were manufactured control sera containing normal levels of protein (approximately 7%) and estriol. Six of the samples were random female patient serum samples having varying protein levels and varying estriol concentrations. Three of the serum samples were obtained from males and contained having no estriol. The final two samples were 4% human serum albuman (HSA) and 7% HSA, both containing no estriol.

The level of estriol in samples 1–9 (manufactured control sera and random patient serum samples) was measured using the following standard reference technique. An extraction solvent was prepared by combining three parts ethyl acetate with two parts hexane. The samples (500$\mu$l) were mixed with extraction solvent (5ml) in test tubes by vortexing. After from 5 to 10 minutes, the mixture separated into layers and 100$\mu$l from the top layer was transferred to another test tube. The transferred portion was evaporated at 37°–40° C. under a stream of dry air. Tracer (1.0ml) and beads (100$\mu$l) were then added to the second test tube and allowed to incubate at room temperature for about 60 minutes. The beads were separated by centrifugation (1500× g for 10 minutes) and counted for one minute. The concentration of estriol was then determined from a standard curve where the standards were subjected to the same extraction technique. In this way, protein interference was minimized and accurate measurement of the absolute level of estriol in the samples was obtained.

Each of the samples was assayed, up to 13 times, using various combinations of the additives ANS, sodium deoxycholate, 23 lauryl ether (Brij ® 35, Sigma Chemical Company), and polyoxyethylene sorbitan mono-oleate (Tween ® 80, Rohm and Haas).

The following protocol was employed. Each sample (10$\mu$l) was added to a test tube (12×75mm). Tracer solution (1.0ml, including the additives, if any) was then added to the tubes and at the same time a separate portion of tracer solution (1.0ml) was added to a Total Counts Tube which was set aside. (Anti-estriol beads (100$\mu$l) were added to each sample tube and the tubes agitated. The tubes were allowed to incubate at room temperature for at least 60 minutes, and then centrifuged at 1500× g for 10 minutes to pack the beads at the bottom of the tube. The supernatants were immediately removed by carefully inverting each tube to pour off the liquid and removing the last drop by gently blotting the tube rim on a paper towel. The tubes, including the Total Counts Tube, were then counted on a suitable radioactive decay monitor for 1 minute and the counts recorded. The level of estriol in the sample was then determined by comparing the (1) ratio of counts in the sample (B) to counts in the 0.0ng/ml estriol standard ($B_o$) with (2) a standard curve generated from standardized samples.

TABLE 1

| ANS | | | none | | none | | none | |
| Sodium | | | none | | none | | none | |
| Deoxycholate | | | none | | 1000 μg/ml | | 2000 μg/ml | |
| Brij ® 35 | | | none | | none | | none | |
| Tween ® 80 | | | none | | none | | none | |
| Sample No. | Protein Level | Estriol* (ng/ml) | $B^+/B_o$ | Measured# Estriol (ng/ml) | $B^+/B_o$ | Measured# Estriol (ng/ml) | $B^+/B_o$ | Measured# Estriol (ng/ml) |
|---|---|---|---|---|---|---|---|---|
| 1 | normal | 8.8 | — | 6.3 | — | 8.9 | — | 8.5 |
| 2 | normal | 14.6 | — | 18.7 | — | 16.6 | — | 15.8 |
| 3 | normal | 25.2 | — | 29.2 | — | 28.2 | — | 28.2 |
| 4 | variable | 8.0 | — | 5.4 | — | 14.6 | — | 16.7 |
| 5 | variable | 7.0 | — | 3.5 | — | 11.1 | — | 12.5 |
| 6 | variable | 8.5 | — | 3.7 | — | 14.0 | — | 15.4 |
| 7 | variable | 10.5 | — | 8.8 | — | 16.6 | — | 18.9 |
| 8 | variable | 14.3 | — | 11.9 | — | 28.2 | — | 32.5 |
| 9 | variable | 26.6 | — | 24.1 | 39.5 | — | 44.0 | — |
| 10 | variable | 0.0 | 129% | — | 104% | — | 99.7 | — |
| 11 | variable | 0.0 | 110% | — | 102% | — | 98.8 | — |
| 12 | variable | 0.0 | 109% | — | 101% | — | 97.0 | — |
| 13 | 4% HSA | 0.0 | 110% | — | 104% | — | 102 | — |
| 14 | 7% HSA | 0.0 | 83% | — | 96.3% | — | 97.6 | — |

| | ADDITIVES | | | | | | | |
| ANS | none | | none | | 20 μg/ml | | 20 μg/ml | |
| Sodium | none | | none | | none | | none | |
| Deoxycholate | none | | 300 μg/ml | | 150 μg/ml | | 30 μg/ml | |
| Brij ® 35 | none | | none | | none | | none | |
| Tween ® 80 | 1000 μg/ml | | none | | none | | none | |
| Sample No. | $B^+/B_o$ | Measured# Estriol (ng/ml) | $B^+/B_o$ | Measured# Estriol (ng/ml) | $B^+/B_o$ | Measured# Estriol (ng/ml) | $B^+/B_o$ | Measured# Estriol (ng/ml) |
|---|---|---|---|---|---|---|---|---|
| 1 | — | 7.7 | — | 9.9 | — | 8.0 | — | 7.8 |
| 2 | — | 15.8 | — | 16.3 | — | 15.4 | — | 15.4 |
| 3 | — | 26.1 | — | 22.9 | — | 25.2 | — | 24.9 |
| 4 | — | 12.8 | — | 11.5 | — | 10.4 | — | 9.6 |
| 5 | — | 10.3 | — | 7.4 | — | — | — | — |
| 6 | — | 12.4 | — | 8.6 | — | 10.3 | — | 9.2 |
| 7 | — | 14.5 | — | 11.1 | — | — | — | — |
| 8 | — | 22.9 | — | 18.7 | — | 17.7 | — | 17.8 |
| 9 | — | ~40 | — | 24.8 | — | 29.6 | — | 26.0 |
| 10 | 103% | — | 118% | — | 104% | — | 104% | — |
| 11 | 101% | — | 113% | — | — | — | — | — |
| 12 | 98.4% | — | 119% | — | 103% | — | 104% | — |
| 13 | 100% | — | 108% | — | 99.4% | — | 102% | — |
| 14 | 93% | — | 87.4% | — | — | — | — | — |

| | ADDITIVES | | | | | | 
| ANS | 20 μg/ml | | 15 μg/ml | | 10 μg/ml | |
| Sodium | none | | none | | none | |
| Deoxycholate | 600 μg/ml | | 300 μg/ml | | 300 μg/ml | |
| Brij ® 35 | none | | none | | none | |
| Tween ® 80 | | | | | | |
| Sample No. | $B^+/B_o$ | Measured# Estriol (ng/ml) | $B^+/B_o$ | Measured# Estriol (ng/ml) | $B^+/B_o$ | Measured# Estriol (ng/ml) |
|---|---|---|---|---|---|---|
| 1 | — | 7.7 | — | 7.1 | — | 7.9 |
| 2 | — | 15.3 | — | 15.8 | — | 17.7 |
| 3 | — | 23.8 | — | 25.2 | — | 26.0 |
| 4 | — | 11.1 | — | 9.5 | — | 9.7 |
| 5 | — | — | — | — | — | — |
| 6 | — | 11.3 | — | 8.6 | — | 8.9 |
| 7 | — | — | — | — | — | — |
| 8 | — | 19.0 | — | 19.3 | — | 19.0 |
| 9 | — | 29.4 | — | 30.0 | — | 30.2 |
| 10 | 102% | — | 106% | — | 110% | — |
| 11 | — | — | — | — | — | — |
| 12 | 99.8% | — | 104% | — | 109% | — |
| 13 | 98.6% | — | 99.8% | — | 103% | — |
| 14 | — | — | — | — | — | — |

| | ADDITIVES | | | | | |
| ANS | 30 μg/ml | | 30 μg/ml | | 30 μg/ml | |
| Sodium | none | | none | | none | |
| Deoxycholate | 300 μg/ml | | 600 μg/ml | | 150 μg/ml | |
| Brij ® 35 | none | | none | | none | |
| Tween ® 80 | | | | | | |
| Sample No. | $B^+/B_o$ | Measured# Estriol (ng/ml) | $B^+/B_o$ | Measured# Estriol (ng/ml) | $B^+/B_o$ | Measured# Estroil (ng/ml) |

TABLE 1-continued

| | | | | | | |
|---|---|---|---|---|---|---|
| 1 | — | 7.6 | — | 8.1 | — | 7.9 |
| 2 | — | 15.5 | — | 15.4 | — | 13.8 |
| 3 | — | 27.1 | — | 26.4 | — | 27.8 |
| 4 | — | 9.9 | — | 11.1 | — | 10.0 |
| 5 | — | — | — | — | — | — |
| 6 | — | 10.0 | — | 10.9 | — | 9.6 |
| 7 | — | — | — | — | — | — |
| 8 | — | 20.7 | — | 20.9 | — | 20.3 |
| 9 | — | 25.6 | — | 31.8 | — | 33.0 |
| 10 | 104% | — | 102% | — | 102% | — |
| 11 | — | — | — | — | — | — |
| 12 | 103% | — | 100.5% | — | 101% | — |
| 13 | 99.9% | — | 99.6% | — | 98.8% | — |
| 14 | — | — | — | — | — | — |

*Measured by extraction reference technique.
+ $\frac{\text{CPM sample}}{\text{CPM 0.0ng/ml estriol}}$
Measured from standard curve.

The results indicate that the combination of a non-ionic detergent (e.g. a polyoxyethylene ether) with a surface active agent inhibits the observed protein interference in the estriol assay. In samples 10-14 having no estriol, the ratio $B/B_o$ should be 100%, that is, equal to the binding predicted by the standard curve at 0.0ng/ml estriol. The percentage of binding, however, is substantially greater than expected in the low and variable protein samples having no additives.

The addition of ANS, sodium deoxycholate, or polyethylene sorbitan mono-oleate (Tween® 80) in the absence of 23 lauryl ether (Brij® 35) corrects the reading at zero estriol levels, but introduces error in the measurement of positive estriol levels. The addition of ANS, sodium deoxycholate or polyoxyethylene sorbitan mono-oleate in combination with 23 lauryl ether corrects the readings at zero estriol levels without degrading the results at positive estriol levels.

Although the best mode contemplated for carrying out the present invention has been herein shown and described, it will be appreciated that variations and modifications may be made without departing from what is regarded to be the subject matter of the present invention.

What is claimed is:

1. In an immunoassay for determining the presence of estriol in samples of human sera, said assay depending on binding between the estriol and a specific binding protein in an assay medium, an improvement comprising adding to the assay medium predetermined amounts of both a polyoxyethylene ether and a surface active agent selected from the group consisting of polyoxyethylenesorbitans, deoxycholate salts, and ANS, said predetermined amounts selected to inhibit protein interference with the specific binding between the estriol and specific binding protein.

2. An immunoassay for determining the presence of estriol in a sample of human sera, the assay involving competitive binding between the estriol and a labeled estriol analog to an immobilized binding protein specific for estriol, said assay comprising:
   combining in an aqueous assay medium, the sample, the labeled estriol analog and the immobilized binding protein in the presence of sufficient amounts of a polyoxyethylene ether and a surface active agent selected from the group consisting of polyoxyethylenesorbitans, deoxycholate salts, and ANS so as to prevent protein interference with specific binding between the binding protein and the labeled estriol analog;
   incubating the mixture for a sufficient time to allow specific binding of the estriol and labeled estriol to the immobilized binding protein;
   separating the immobilized binding protein from the assay medium; and
   detecting the amount of labeled estriol bound to the immobilized binding protein or the amount remaining unbound in the assay medium.

3. An immunoassay assay as in claims 1 or 2, wherein the polyoxyethylene ether is added to a final concentration in the range from about 30 to 1500µg/ml and the surface active agent is ANS added to a final concentration of from about 1 to 100µg/ml of assay medium.

4. An immunoassay as in claims 1 or 2, wherein the polyoxyethylene ether is added to a final concentration in the range from about 30 to 1500µg/ml and the surface active agent is either a polyoxyethylenesorbitan or a deoxycholate salt added to a final concentration of from about 100 to 5000µg/ml.

5. An immunoassay as in claims 1 or 2, wherein the polyoxyethylene ether is added to a final concentration in the range from about 270 to 330µg/ml and the surface active agent is ANS added to a final concentration of from about 10 to 25µg/ml of assay medium.

6. An immunoassay as in claims 1 or 2, wherein the polyoxyethylene ether is added to a final concentration in the range from about 270 to 330µg/ml and the surface active agent is either a polyoxyethylenesorbitan or a deoxycholate salt added to a final concentration of from about 500 to 2500µg/ml.

7. An immunoassay as in claims 1 or 2, wherein the labeled estriol, polyoxyethylene ether and surface active agent are combined in a tracer solution prior to addition to the assay medium.

8. An immunoassay as in claims 1 or 2, wherein the polyoxyethylene ether is selected from the group consisting of lauryl ether, cetyl ether, oleyl ether, stearyl ether, and tridecyl ether.

9. An immunoassay as in claims 1 or 2, wherein the polyoxyethylenesorbitans are selected from the group consisting of polyoxyethylenesorbitan mono-oleate, polyoxyethylenesorbitan mono-palmitate, polyoxyethylenesorbitan mono-stearate, and polyoxyethylenesorbitan trioleate.

10. A kit for performing an immunoassay to determine the presence of estriol in human sera, said kit comprising:
   a tracer comprising radioactively labelled estriol;
   a reagent comprising a binding protein specific for estriol immobilized on polymeric particles;

sufficient amounts of a polyoxyethylene ether and a surface active agent selected from the group consisting of polyoxyethylenesorbitans, deoxycholate salts, and ANS to inhibit protein interference in performing the assay when added to the assay medium; and a container for holding said tracer, reagent, and polyoxyethylene ether and surface active agent, where the tracer and reagent are stored separately.

11. A kit as in claim 10, wherein the polyoxyethyleneether and surface active agent are combined with the tracer.

12. A kit as in claim 10, wherein the polyoxyethylene ether is selected from the group consisting of lauryl ether, cetyl ether, oleyl ether, stearyl ether, and tridecyl ether.

13. A kit as in claim 10, wherein the polyoxyethylenesorbitans are selected from the group consisting of polyoxyethylenesorbitan mono-oleate, polyoxyethylenesorbitan mono-palmitate, polyoxyethylenesorbitan mono-stearate, and polyoxyethylenesorbitan trioleate.

14. A kit as in claim 10, wherein the polyoxyethylene ether is 23 lauryl ether and the surface active agent is polyoxyethylenesorbitan mono-oleate.

15. A kit as in claim 10, wherein the polyoxyethylene ether is 23 lauryl ether and the surface active agent is sodium deoxycholate.

16. A kit as in claim 10, wherein the polyoxyethylene ether is 23 lauryl ether and the surface active agent is ANS.

17. A kit as in claim 10, wherein the tracer and specific binding protein are present in separate buffer solutions.

18. A kit as in claim 10, wherein the tracer and receptor are lyophilized.

* * * * *